(12) United States Patent
Morgan

(10) Patent No.: US 7,441,442 B2
(45) Date of Patent: Oct. 28, 2008

(54) SYSTEM FOR DETERMINING THE DISPLACEMENT OF A MOVABLE MEMBER

(75) Inventor: Barry Alfred Morgan, Tintagel (GB)

(73) Assignee: Kernow Instrument Technology Limited, North Petherwin, Launceston, Cornwall (GB)

( * ) Notice: Subject to any disclaimer, the term of this patent is extended or adjusted under 35 U.S.C. 154(b) by 0 days.

(21) Appl. No.: 11/661,481

(22) PCT Filed: Aug. 26, 2005

(86) PCT No.: PCT/GB2005/003363

§ 371 (c)(1),
(2), (4) Date: Feb. 27, 2007

(87) PCT Pub. No.: WO2006/021808

PCT Pub. Date: Mar. 2, 2006

(65) Prior Publication Data

US 2007/0256507 A1   Nov. 8, 2007

(30) Foreign Application Priority Data

Aug. 27, 2004   (GB) ................................ 0419152.4

(51) Int. Cl.
*G01N 11/14* (2006.01)

(52) U.S. Cl. ..................................... 73/54.43; 73/54.28

(58) Field of Classification Search ..... 73/54.23–54.28, 73/54.43
See application file for complete search history.

(56) References Cited

U.S. PATENT DOCUMENTS

| | | | | |
|---|---|---|---|---|
| 4,499,753 A | * | 2/1985 | Carr | 73/54.35 |
| 4,524,611 A | * | 6/1985 | Richon et al. | 73/54.35 |
| 4,630,468 A | * | 12/1986 | Sweet | 73/54.43 |
| 5,237,229 A | * | 8/1993 | Ohishi | 310/90.5 |
| 5,874,665 A | * | 2/1999 | Larsson | 73/54.28 |
| 6,024,491 A | * | 2/2000 | Bak | 384/106 |
| 6,114,788 A | * | 9/2000 | Vuillemin (Muller) et al. | 310/90.5 |
| 6,177,997 B1 | * | 1/2001 | Blumenstock et al. | 356/625 |
| 6,938,464 B1 | * | 9/2005 | Bi | 73/54.28 |
| 2004/0011149 A1 | * | 1/2004 | Carroll | 73/866.1 |

* cited by examiner

*Primary Examiner*—Edward Lefkowitz
*Assistant Examiner*—Punam Patel
(74) *Attorney, Agent, or Firm*—Kimberly A. Chasteen

(57) ABSTRACT

A means for simultaneous determination of the radial and angular vectors of rotary motion of a body relative to a single reference axis, by measurement of the common aid differential states of three position detectors and, together with an axial position detector, thus to allow the measurable modulation of magnetic devices such as to provide measurable vector forces to support that body against the vector effects of any external forces that tend to change its position relative to the reference axis, in the absence of any contact between the rotor and the combined system of sensors and magnetic devices.

11 Claims, 2 Drawing Sheets

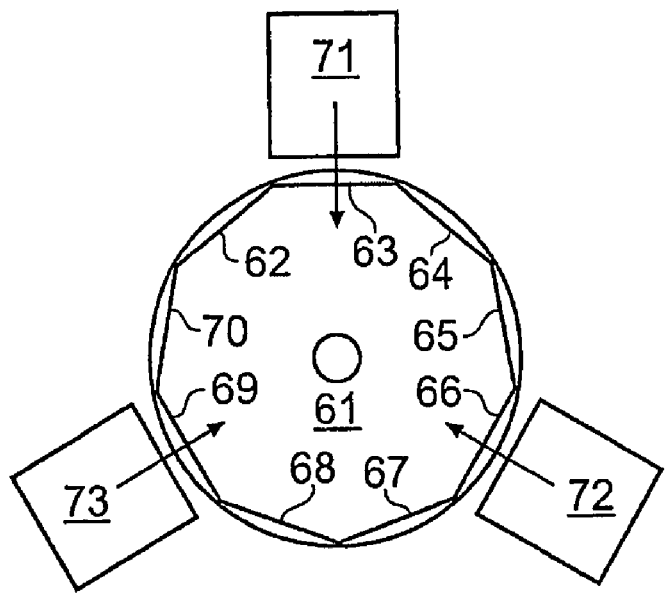
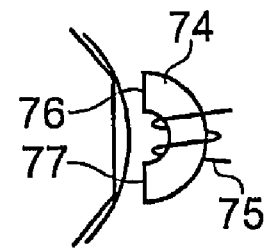
Fig. 3a
Fig. 3
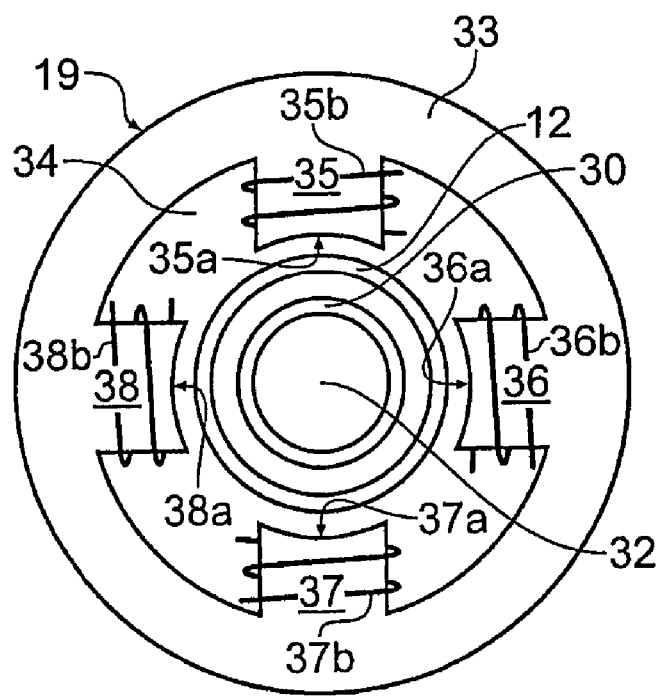
Fig. 4

SYSTEM FOR DETERMINING THE DISPLACEMENT OF A MOVABLE MEMBER

BACKGROUND OF THE INVENTION:

The present invention relates to a system for determining the forces exchanged by and/or the displacement of a movable member and particularly, although not exclusively, the linear and angular position of a body with respect to an axis of reference. The present invention finds particular utility as apparatus for the determination of the deformation properties of materials. Embodiments of the present invention may comprise contactless magnetic means for application of defined vector forces to a suspended body, and contactless means for the determination of vector displacements of that body. The system may include means for measuring time, to enable the accurate characterization of material deformation events, especially, but not exclusively, under low and high-pressure, conditions.

The study of material deformation events is common to many scientific and technological fields and precise description and measurement of such events has subsequently led to great improvement in materials production and usage.

Measurement of the deformation that results from a known applied force (stress) is fundamental to most such studies and usually expressed as the deformation (strain) induced by an applied stress. A contemporaneous measure of time provides an additional insight into most such deformation events.

Thus for example, time-dependent permanent (plastic) deformation or creep can occur when classical Hookean solid materials are subjected to stress below the proportionality limit over long periods.

The deformation of simple liquids, may be regarded as continuous permanent deformation (flow) and is expressed in terms of a shearing stress and a shear strain rate, while more complex visco-elastic materials may exhibit a degree of recoverable deformation that itself is time dependent.

Thixotropic behaviour is both rate and duration dependent.

Of the different instruments devised for deformation measurement, many deploy a common principle.

A known force is applied to a geometrically defined body in contact with a test material supported in a geometrically defined manner, so as to resist the applied force or stress. A measurement of the resultant material deformation as a linear or angular displacement is used to quantify the strain induced.

In liquids the strain is expressed as a rate; the velocity gradient between the adjacent shear planes.

Such simple devices as penetrometers which utilizes a gravity-driven plunger to apply force share the above common principle with complex instruments such as rotational rheometers and in consequence, share similar potential limitations to measurement and common sources of error.

In such instruments, the line of action and magnitude of the applied force must be defined (a force vector) and this usually calls for friction bearing or guides.

Friction arising from these bearings limits the accuracy of the applied force, while bearing-alignment error corrupts the geometric accuracy of the vector, as will errors in alignment of the surface which supports the test material.

A further common source of error or limitation lies in the accuracy and resolution of the measurement of displacement induced in the test material.

Others factors which may affect the integrity of test results, are those which might alter the physical or chemical nature of the test material.

Temperature and pressure, for example, can have a significant influence and should be at least monitored and preferably controlled during the test; indeed, in some cases, the temperature and pressure conditions of material storage prior to testing can significantly alter its subsequent deformation behaviour.

Sample changes due to the loss of volatile constituent are also a potential source of error.

Thus for an idealized test, it is required that:
1. the force application member (such as a plunger or rotary bobbin) has a geometrically accurate surface
2. the magnitude of the force applied to the application member should be known with the greatest possible accuracy
3. its subsequent movement should be controlled to close tolerances without any friction
4. the sample support surface should itself be geometrically accurate and its spatial relationship to the line of action of the actuator should also be constrained to close tolerances
5. the test conditions of temperature and pressure should be controlled and volatile loss prevented.
6. time is accurately measured during the test period.

The above represents a 'minimal ideal' but some complex forms of material behaviour may also require that sample deformation tendency be measured as more than one vector; such as investigation of normal stress effects that may be exhibited, for example, during extrusion processes as die swell.

Another common requirement is for repeated reversal of the direction of stress application, as in oscillatory testing, so as to reveal visco-elastic behaviour.

Other chemical and physical changes may occur as a result of testing and might be usefully indicated by contemporaneous measurement of hydrogen ion concentration (pH) or electrical conductivity for example.

In attempting to meet the above ideals, we have conceived a device based upon the contactless support of an appropriately shaped member by means of modulated magnetic forces, with the forces required to move the actuator being continuously measured or at least determined. Any movements (linear or rotary) of the member are also measured using non-contact position sensors and thus the member may be supported and moved, while free of any contact with other components of the device.

It may similarly be supported while enclosed within a chamber, without touching the chamber walls.

In this way, we avoid friction errors and enable the test member to have contact solely with the test material which may also be present within this chamber.

Pressure conditions may thus be controlled during testing and volatile loss avoided.

Rheometers may be regarded as among the more complex instruments used for measurement of material deformation and flow properties.

Rotary devices are commonly used as viscometers and rheometers; shear stress being defined in terms of a turning moment or torque and shear strain defined by an angular displacement.

A simultaneous measure of time allows for rate computation and determination of the rate of change of velocity of the shear planes within the sample with respect to the distance between the planes (shear strain rate). The coefficient of viscosity is the constant of proportionality that relates shear stress and shear strain rate.

While rotary viscometers and rheometers are both capable of the required determination of shear stress, shear strain and time, rheometers are distinguished by greater range, accuracy and flexibility in the mode of application and measurement of these parameters. Of particular significance is the ability to measure very small increments of shear stress and shear strain to allow investigation of limiting sample characteristics.

A further valuable rheometric function lies in the capability for controlled reversal of rotational direction (oscillation) which enables measurement of recoverable deformation (visco-elastic) behaviour in liquids and semi-solids. Rheometers also allow attenuation or adjustment of the defined applied variable (shear stress or shear strain) with respect to time and other dependent or independent measured variables such as, temperature, pressure, torque, angular displacement, pH, electro-potential and electro-conductivity, that might affect or be affected by, the sample under test.

The flow conditions that may be induced between adjacent defined surfaces, such as between cones, plates and cylinders, for example, have been well defined and are widely accepted as offering optimal compromises for accurate measurement.

However, such states of defined deformation and flow assume a constant radial or annular relationship between the adjacent surfaces whether or not there is relative angular displacement about a common axis.

Hence, high levels of dimensional accuracy are required both in the conformation of the components and in the maintenance of their juxtapositional relationship when static and during rotation.

As described earlier, any bearing system deployed to support the movable component or components therefore requires the best possible dynamic stiffness, while the precise application and measurement of angular displacement and torque can be corrupted by friction or drag arising from the support or drive mechanism of the instrument.

Thus, much instrument development has been aimed at improving bearing performance, especially the reduction or elimination of the deleterious effect of friction and drag.

To this end, non-contact devices have been designed in which bearing surfaces are separated by means of air currents (air bearings) or magnetic repulsive forces (magnetic bearings).

Since air bearings require that a constant uniform flow of air be supplied, they are not well suited to function within an environment that is subjected to very low or very high pressure or changes in pressure.

Unmodulated (passive) magnetic forces of attraction and repulsion demonstrate inherent instability when applied to bearing function and thus require the addition of other means to constrain that instability.

The use of electro-magnets in which the electric power is modulated in direct response to changes of position of the supported component such that the consequent change in magnetic force serves to adjust the position of that component so as to attain its required spatial location is known.

It follows therefore, that any active magnetic bearing must comprise both the electro-magnetic modulation means and means for detecting the position of the supported component, linked together to form a closed-loop negative feedback system. The functional efficiency and the accuracy attained in constraining the supported component within closely defined spatial limits, depends largely upon the response rate of the feedback loop.

Most rotary viscometers and rheometers provide support for the rotating components which are in contact with the sample under test, by the provision of a supporting spindle attached to the sample-contact component and extending beyond the sample zone to an attached bearing. Any component used to measure torque or rotation of the support spindle is also similarly located outside the sample medium.

There are however alternative examples of viscometer design which have effectively eliminated the need for a discrete supporting spindle, by submerging a geometrically defined element entirely within the sample material which is contained within a chamber, such that the sample medium entirely invests the bobbin. These instruments rely upon externally generated magnetic forces or internal sample forces such as buoyancy or pressure gradients, induced in the sample by rotation or oscillation, to provide support and location of the bobbin, free of contact with the sample chamber or any other component of the instrument.

One such prior art example describes a visco-densimeter, in which the mass of a magnetically sensitive cylindrical bobbin is supported in vertical axial alignment by an active magnetic suspension system in opposition to gravity.

The spatial position of the bobbin is detected optically so as to provide the required reference signal for the feedback loop.

This stable support system allows suspension the cylindrical bobbin out of contact with the walls of a larger static encapsulating concentric cylinder which may be filled with test material to form a sample chamber provided with closure means.

A well defined annulus is thus created between the bobbin and the concentric sample chamber, thus enabling constraint of the shearing conditions as the cylindrical bobbin is rotated.

A contactless means of rotation is provided by a variable, rotating electro-magnetic field generated within static coils, peripheral to the sample chamber. Rotation of the bobbin is enabled by means of the well established principles of an eddy current drive system. The turning moment thus induced in the bobbin is opposed by viscous drag imparted by the test sample and the resultant rotation attained by the bobbin is detected by a small sensing coil located within the sample chamber, which responds to a magnet fixed within the bobbin. The frequency and current applied to the drive system may then be compared with the bobbin rotation so as to derive a measure of viscous drag in the sample.

Apart from the closure mechanism for the sample chamber, the bobbin is the only component capable of spatial movement and that motion is limited to an angular displacement relative to the concentric sample chamber, about the common axis. By providing contactless measurable axial support and measurable rotational drive within a sealed sample chamber, this design offers much of the competence identified as desirable for an 'idealised' instrument; absence of unwanted friction drag, well defined conformation within the sample measurement zone, the option of controlling the pressure conditions within the sample chamber and the elimination of volatile sample loss and containment of sample hazard.

However, the prior art example cited above, has functional limitations in that the rotation detection system demonstrates limited angular resolution, the optical position detector is not suited for use with opaque sample media, the sample chamber wall thickness and thus the pressure limit is restricted by the need for magnetic transparency and the axial orientation of the magnetic bearing support constrains operational alignment of the instrument with respect to gravity.

It is current practice in commercial rheometers to use optical detection for determination of angular displacement of rotary components and this achieves very high levels of resolution with systems which are often described as optical code wheels. Such devices are unsuited for use when invested by an optically opaque medium.

Alternatives to optical sensing have been tried elsewhere in devices suitable for detection of linear or angular displacement, usually called proximity sensors, including the use of such sensors as the required position-detection components of magnetic bearings.

Contactless proximity sensors, capable of precise position sensing when the intervening space between the sensor and the detected body contains an optically opaque medium, include those responsive to changes in electrical capacitance, electrical inductance and magnetic flux density (Hall Effect devices), however, the prior art has not demonstrated the use of these for the precise measurement of angular displacement as required for the aforementioned 'ideal instrument'.

SUMMARY OF THE INVENTION:

The present invention is a means simultaneous determination of the radial and angular vectors of rotary motion of a body relative to a single reference axis, by measurement of the common aid differential states of three position detectors and, together with an axial position detector, thus to allow the measurable modulation of magnetic devices such as to provide measurable vector forces to support that body against the vector effects of any external forces that tend to change its position relative to the reference axis, in the absence of any contact between the rotor and the combined system of sensors and magnetic devices. Measurement of the vector forces applied to the suspended b>dC and its resultant vector displacements, provides the functional basis of a device suitable for measuring the effects of mechanical interaction between that body and any spatially constrained sample material in contact with the b>dC, with respect to the applied vector stresses and resultant vector strains that exist as a result of any shearing or grinding abrasion in indention deformation or cutting action applied by the rotor to that material during a measured time period. The basic device being consistent with the functions of a rotary viscometer or rheometer or appropriate for use in evaluating the action of a drilling or milling cutter, even when the sample material and the b>dC are confined within a chamber subjected to low or high internal pressure with respect to the external environment. Such confinement also avoids volatile loss of constituents from the sample material and any environmental hazard arising from such loss.

The present invention seeks to address the problems of the prior art and to provide, in particular, a sensing means able to measure the spatial position of a body with respect to its axes of linear and angular displacement, so as to allow contactless detection and control of the linear and angular displacement of that body in a manner suitable for the measurement of the deformation and flow properties of materials, especially when the body is suspended within a chamber that may be filled with test material and, if required, may be subjected to very low or very high internal pressures.

Accordingly, a first aspect of the present invention provides a contactless magnetic rotary bearing for a rotary machine having a rotor and a stator, comprising a magnet assembly rotatable about an axis of rotation about which are located at least three fixed bearing coils having substantially radial axes at approximately equiangular spacing around the said axis of rotation, and at least three proximity sensors also equiangularly spaced around the said axis of rotation, the output of each sensor being used to determine the current supplied to a respective said bearing coil whereby to maintain the rotor centralized with respect to the stator. Using such a bearing the low friction requirement of rheometers may be addressed by the use of contactless magnetic bearings, rather than mechanical coupling. All active bearing designs must incorporate positional sensing means to generate feedback signals corresponding to instabilities in the rotor alignment. These feedback signals allow generation of corrective impulses in the electromagnets that locate the rotor. This feedback loop system must operate at high speed in order to minimize rotor wobble and must also be free from any tendency to self induced vibration/oscillation at all required speeds of rotation. These requirements are met in the bearing of the invention.

In a preferred embodiment of the invention sensors are circumferentially in register with respective bearing coils. For use in a rheometer or other device the output from at least one sensor may be used to provide an angular position signal. This may be achieved, for example, by providing at least one detectable feature on the rotor or a component attached thereto the periodic passage of which past the stationary sensor provides a recognizable periodicity in its output signal for the purpose of determining the angular position of the rotor. For increased accuracy the output from two or more sensors may be summed to provide the angular position signal.

In another aspect, the present invention also comprehends a device for measuring the deformation properties of a material sample, the device comprising a surface for constraining a sample, a rotor in controlled spatial relationship to the sample surface, at least one active contactless magnetic bearing operable to support the rotor, drive means operable to apply a turning moment to the rotor, means for generating a signal indicative of the angular position of the rotor, and means for determining a deformation property of a sample in contact with the rotor.

In this aspect of the invention the or each contactless magnetic bearing may comprise two or more coils.

It will be appreciated that in situations where there is more than one magnetic bearing, each contactless magnetic bearing may have the same or a different number of coils assembled in a regular homo-polar arrangement around the rotor.

The device may further comprise means operable to determine the angular velocity of the rotor. Such calculation means may form an integral part of the device or may comprise a non-integral unit for connection with the device in use.

In a preferred embodiment, the calculation means is operable to calculate the deformation properties of the sample from the applied torque, the directional angular displacement and the measured time. In addition, other relevant factors such as sample temperature and pressure may be simultaneously combined within the calculation means. The result of such calculation being provided as an output signal or signals, such as numerical values, a graphical display or any other suitable output providing the operator of the device with an indication of the deformation properties of the sample under the conditions applied during the test period. Embodiments may be provided, for example, in which the output may indicate only whether a sample does or does not fall within a predetermined or selected range.

BRIEF DESCRIPTION OF THE DRAWINGS

One embodiment of the present invention will now be described by way of example only and with reference to the accompanying drawings, in which:

FIG. 3 is a cross-sectional view taken on the line III-III of FIG. 2; and FIG. 4 is a cross-sectional view taken on the line IV-IV of FIG. 2.

DETAILED DESCRIPTION OF THE PREFERRED EMBODIMENT

Figure 1:
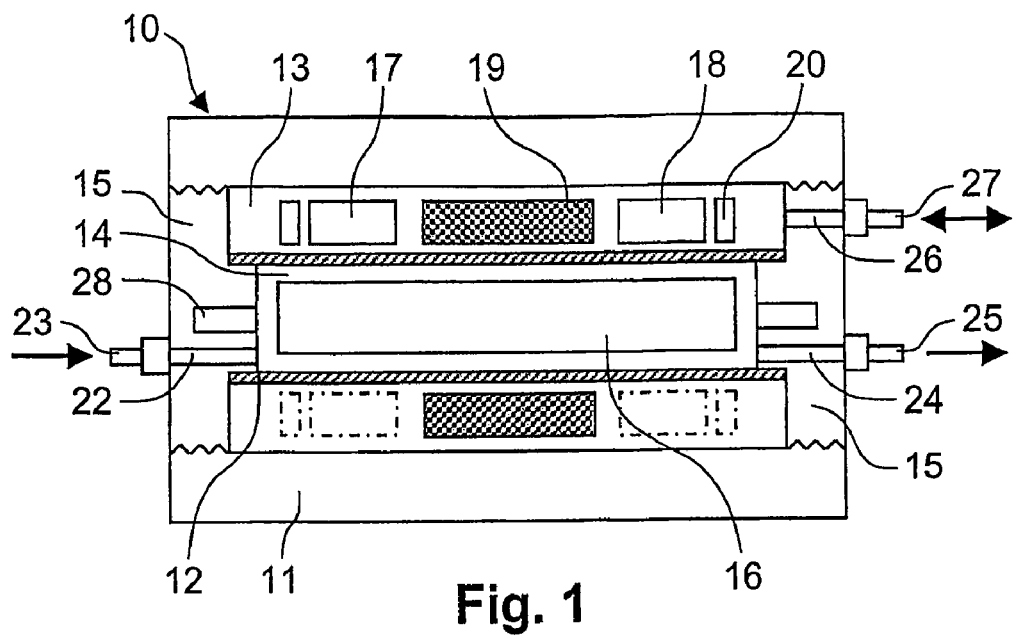
FIG. 1 is an axial-sectional view of a first embodiment of a device in accordance with the present invention.

Referring first to FIG. 1, the device 10 shown is designed for determining the deformation properties of sample materials, and includes an outer pressure vessel 11 capable of resisting the high pressures that may be applied to any sample under test.

The interior of the pressure vessel 11 is partitioned by a cylindrical sleeve 12 that separates an inner chamber 14, that may contain sample material from an outer chamber 13 that contains an inert fluid. The ends of the sleeve 12 are secured to the end plugs 15 of the pressure chamber 11 so that the outer chamber 13 is sealed from the inner chamber 14. The sleeve 12 is a relatively thin-walled tube of magnetically transparent material the function of which will be described in more detail below. Within the inner chamber 14 is a rotor 16 the construction and function of which will be described in more detail below. The rotor 16 is suspended in the interior chamber 14 out of contact with the sleeve 12 by two sets of magnetic contactless bearings 17, 18. When in horizontal alignment as shown, passive axially directed magnetic forces arising from the magnetic bearings 17, 18, constrain the rotor to an axially central position, out of contact with the end plugs 15 of the pressure chamber. For use in a vertical alignment, additional magnetic devices may be housed within the end plugs 15 to provide additional axially directed forces opposing the effect of gravity. A turning moment or torque is applied to the rotor by stator windings 19 in a manner which will be described in more detail below, and the radial and angular position of the rotor 16 is determined by a sensor means 20. The magnetic contactless bearings 17, 18, the drive coils of the stator 19 and the sensor means 20 for detecting the radial and angular position of the rotor 16 are all housed in the outer chamber 13. The wall thickness of the sleeve 12 is made as small as possible in order to minimize the gap between the stator coils 19 and the co-operating components of the rotor 16. This also applies to the separation between the rotor 16 and the magnetic bearings 17, 18 and, to the same extent to the sensor means 20, which detects the radial and angular position of a component 21 of the rotor 16, while retaining a prescribed optimal annular gap between the inner surface of the sleeve 12 and the outer surface of the rotor 16. In practice there is a conflict between the ideal minimum gap for low power consumption/heat generation and the need for a significant gap between the rotor and the sleeve which is filled with the test sample. From a theoretical point of view the smaller the gap the better, but in practice there are problems with very small sample gaps, in particular any machining errors in the sleeve surface or rotor surface may introduce a significant, measurable, effect on the sample deformation process. Further, many test samples contain internal "structure" such as partially developed crystal matrices. If the sample gap is too small then such internal structures are physically constrained with a concomitant alteration in the behaviour of the sample that does not represent its usual state.

The pressure vessel 11 has sample transfer passages 22 and 24 in the end plugs 15, access to which is gained via connectors 23 and 25 on the outside of the end plugs 15 of the pressure vessel 11. Via these connectors a sample material (which may be a gas or a liquid or a paste or other non-solid material, can be introduced into the interior chamber 14 so as to invest the rotor 16. In addition, these connectors allow measurement and control of the pressure conditions within the inner chamber 14. Because the wall of the sleeve 12 is thin pressure equalization is required in order to avoid distorting the sleeve 12, and in this embodiment this is achieved by means of a pressure equalization passage 26 which opens at one end into the outer chamber 13 and communicates with a connector 27. Via this connector, pressure may be applied to the inert fluid in the outer chamber 13 so as to allow pressure equalization between the inner and outer chambers 14, 13 thereby avoiding stresses to the sleeve 12 without allowing communication between these two chambers.

Figure 2:
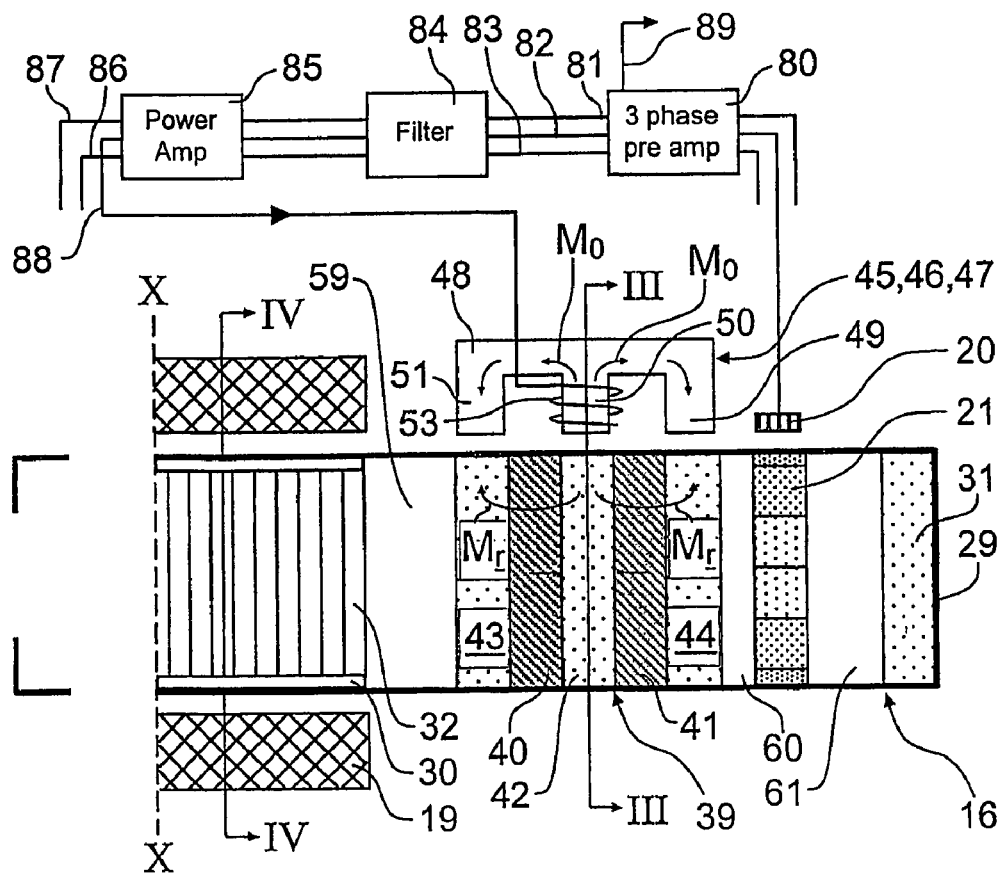
FIG. 2 is an enlarged partly block schematic and partly axial-sectional view of a part of the embodiment of FIG. 1.

Turning now to FIG. 2 the structure of the rotor and of the magnetic bearings and stator, as well as that of the sensor means are described in more detail.

It will be appreciated that, for convenience of description, only one end of the rotor is described here, namely that part from a central region to one end, it being understood that the portion of the rotor 16 on the other side of the mid line is a mirror image thereof.

The rotor 16 comprises an outer magnetically transparent coating 29, inside which lies a copper tube 30, extending from a mid line X-X.

Within the copper tube 30, starting from the mid line X-X the rotor comprises a stack of iron laminations 32 in the form of iron discs. An aluminum spacing disc 59 separates the laminations 32 from the magnetic components 39. The laminations 32 constitute the drive component of the rotor which is surrounded by a stator 19 in the form of iron laminations 33 the shape of which is illustrated in FIG. 4, from which it can be seen that each lamination 33 is in the form of a disc having a central opening 34 with four radially inwardly projecting limbs 35, 36, 37 and 38. The radially inner face of the projections 35-38, identified 35a-38a, are concavely arcuately curved in order closely to engage against the sleeve 12 which separates the outer chamber 13, in which the stator 19 is located, from the inner chamber 14 housing the rotor.

The radially inner projecting limbs 35-38 of the stator laminations 33 bear respective coils 35b-38b which are connected together in opposite phases to form part of an eddy current induction motor driven with two 90° phases to cause a turning moment or torque to be applied to the drive component of the rotor 16. The magnitude of the applied torque is proportional to the frequency and magnitude of the pseudo sine wave currents driving the coils 35b-38b (in the absence of load).

Returning now to FIG. 2, the magnetic bearing component assembly 39 comprises two axially magnetized disc magnets 40, 41 separated by a ferromagnetic pole piece 42, also in the form of a disc of the same shape, with two further pole pieces 43, 44 on either side of the respective magnets 40, 41.

Axially in register with the magnet assembly 39 is a set of homopolar electromagnets 45, 46, 47 only one of which (45) is visible in FIG. 2 as they are equiangularly spaced around the periphery of the rotor, at 120° to one another. The homopolar magnets 45, 46, 47 comprise an array of ferrous metal stacked laminations 48 of E-shape with the three limbs 49, 50, 51 in axial register with the pole pieces 44, 42, 43, respectively of the magnet assembly 39. A copper coil 53 is wound around the central limb 50 of the E-shape stacked lamination core to generate a magnetic flux path as shown by the arrows $M_o$ and $M_r$.

The static electromagnets 45, 46, 47 and the magnetic bearing component assembly 39, constitute an inherently magnetically unstable system that may be rendered stable by modulation of the magnitude and direction of the current supplied to the coils 53 and thence the resultant magnetic flux acting upon the rotor magnetic bearing assembly 39. This modulation of the current is made in response to radial displacement signals received from sensor means 20.

For this purpose the rotor 16 is provided with a ferrite disc 21 separated from the pole piece 44 by an aluminum disc 60.

The outer surface of the ferrite disc 21 is separated by an additional aluminum disc 61 from a ferromagnetic pole piece 31 at the outermost end of the rotor. This latter pole piece is, however, optional. Perturbation of the radial position of the rotor, causes changes in the differential output from the three sensors 20. The resonant frequency of each sensor changes as the gap between the ferrite disc 21 and the sensor pole tips 76, 77 (see FIG. 3a) alters with changing radial position of the rotor. As the sensor moves towards or away from its resonant condition, the amplitude of the voltage across the sensor coil varies and thus provides a signal for the modulation of current supplied to the static electromagnets.

In addition, the same sensors in common mode operation provide a signal representing the angular position of the rotor.

The ferrite disc 21 can be seen more clearly in FIG. 3 to have nine "flats" 62, 63, 64, 65, 66, 67, 68, 69 and 70 which, as will be appreciated from FIG. 3, provides a symmetrical configuration in relation to three sensors 71, 72, 73 each of which, as can be seen from FIG. 3a inset in FIG. 3, comprises a generally semi-circular ferrite element 74 having a coil 75 around its bight portion. The end faces or pole tips 76, 77 of its end limbs face the periphery of the ferrite disc. The sensors 71, 72, 73 are located radially outwardly of the sleeve 12 in the outer chamber 13 in the pressure vessel 11, whilst the ferrite disc 21 is located within the inner chamber 14 as a component of the rotor 16. The number of flats may in fact be a different multiple of the number of sensors. The sensors include coils which are supplied by an oscillator operating at a fixed frequency just offset from the resonant frequency of the sensor. The resonant frequency of each sensor changes as the flats on the ferrite disc 21 pass the sensor pole tips 76,77. As the sensor moves towards or away from its resonant condition, the amplitude of voltage across the sensor coil varies and thus provides a signal whose amplitude itself represents the angular position of the rotor.

These signals are individually supplied to an assembly of three pre-amplifiers 80, the three individual outputs of which are supplied on lines 81, 82, 83 to an assembly of three filters 84. These filters supply respective power amplifiers within a power amplifier assembly 85, the three outputs of which 86, 87, 88 are supplied to respective electromagnet coils 53 of a respective magnetic bearing whereby to vary the centering force to establish rapid centering of the rotor in response to any perturbing radial displacements.

The three pre-amplifiers 80 also have a common output line 89 representing the sum of the three signals from the sensor coils 71, 72, 73 which can be used to determine the angular position of the ferrite disc 21 from the amplitude of the signal. This arrangement automatically compensates for signal strength variation providing a single output signal the amplitude of which represents the angular position of the ferrite disc 21 and thus of the entire rotor 16.

In use of the device described above, a sample to be tested is supplied to the connectors 23 and 25, flowing through the interior of the inner chamber 14 around the rotor 16. Because the magnetic bearings 17, 18 hold the rotor 16 in position without contact with any other component the only contact the rotor experiences is with the fluid of the sample contained within the chamber 14. Contact between the sample and the rotor can thus produce a frictional force opposing the effect of any turning moment or torque applied to the rotor by the eddy current induction motor described earlier. Since this applied torque and any resultant angular displacement of the rotor are known, any effect upon the rotor due to contact with the sample may be determined in a manner entirely in accord with and comparable to the operation of most of the widely available rotary viscometers and rheometers and thus the deformation and flow properties of the sample may be evaluated.

It will be appreciated that the external size, shape and finish of the rotor 16 and the shape and finish of the internal surface of the sleeve 12 may be varied to accord with the nature of the test sample and the requirements of the test conditions. In one such example, the longitudinal axial outer surface of the rotor and the internal surface of the sleeve may be fabricated with a striated or fluted form so as better to contact the sample material. As a further example, each end surface of the rotor may be extended into a conical form with the apices directed toward the respective flat inner surfaces of the end plugs 15. The resultant shape of the sample chamber 14 thus being more precisely defined in terms of the shearing action of the rotor upon the sample.

Loading and cleaning the sample chamber is very simple and can be easily automated. For this reason operation can be fully software controlled and does not require the intervention of a skilled technician as is common with many prior art devices.

Moreover, by virtue of this radical design, there is now an opportunity for deployment in many completely new situations where no prior art rheometer could be used. One example of this is for so-called "down-hole logging" where the robust simplicity of the device would allow remote data capture in the very challenging environment of an oil well bore.

Since only the outer surface of the rotor 16 and the internal surface of the walls of the central chamber 14 are exposed to the test sample, damage to components of the device due to exposure to corrosive samples or sample vapours is minimized or eliminated.

Due to the design of the device 10, wear and tear is predominantly confined to the rotor 16 and the walls of the central chamber 14, both of which can made of or coated with corrosion/wear resistant materials and, if necessary, easily replaced without the need for high precision engineering.

Although aspects of the invention have been described with reference to the embodiments shown in the accompanying drawings, it is to be understood that the invention is not limited to those precise embodiments and that various changes and modifications may be effected without further inventive skill and effort.

What is claimed is:

1. A system for determining the forces acting on a movable member in which the member is suspended out of contact with any stationary component of the system and entirely surrounded by a sample of material to be tested between which and the movable member forces are exchanged in use of the system, the system comprising:
   an outer housing;
   a cylindrical sleeve for retaining the sample of material, said sleeve disposed within said outer housing;
   a rotor forming the movable member and disposed for concentric rotation within the sleeve;
   means for supplying the sample of material to be tested at a pressure to the interior of the sleeve;
   means for supplying a pressurized fluid to the outer housing to surround the sleeve and balance the pressure of the sample of material to be tested within the sleeve;
   magnetic contactless bearings disposed within the housing outside the sleeve to suspend the rotor within the sleeve;
   a stator disposed within the housing and outside the sleeve to impart a turning moment to the rotor; and
   means disposed within the housing and outside the sleeve for sensing the radial and angular position of the rotor.

2. A system as claimed in claim 1, in which there are provided means for causing the said fluid to flow over the movable member in use of the system.

3. A system as claimed in claim 1, in which the rotor comprises an outer magnetically transparent coating and an inner copper tube.

4. A system as claimed in claim 3, in which the rotor comprises a stack of iron laminations within the copper tube.

5. A system as claimed in claim 1, in which the stator comprises laminations, each lamination being a disc having a central opening with four radially inwardly projecting limbs.

6. A system as claimed in claim 1, in which the rotor comprises a magnet bearing component assembly, the magnet bearing component assembly comprising two axially magnetized disc magnets separated by a ferromagnetic disc pole piece.

7. A system as claimed in claim 6, further comprising two ferromagnetic disc pole pieces disposed on either side of the two axially magnetized disc magnets.

8. A system as claimed in claim 6, in which the system further comprises a bearing stator, the bearing stator comprising a set of homopolar electromagnets.

9. A system as claimed in claim 8, in which each homopolar magnet comprises an array of ferrous metal stacked E-shaped laminations, each E-shaped lamination having three limbs extending radially inwards towards the rotor.

10. A system as claimed in claim 9, in which the E-shaped laminations are axially aligned with the two axially magnetized disc magnets in the rotor.

11. A system as claimed in claim 10, in which a copper coil is wound around the central limb of the E-shaped stacked lamination.

\* \* \* \* \*